(12) United States Patent
Morishima et al.

(10) Patent No.: US 7,348,125 B2
(45) Date of Patent: *Mar. 25, 2008

(54) OPTICAL INFORMATION RECORDING MEDIUM AND NOVEL IMMONIUM COMPOUND

(75) Inventors: Shinnichi Morishima, Kanagawa (JP); Michihiro Shibata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 22 days.

This patent is subject to a terminal disclaimer.

(21) Appl. No.: 10/201,973

(22) Filed: Jul. 25, 2002

(65) Prior Publication Data

US 2003/0114710 A1  Jun. 19, 2003

(30) Foreign Application Priority Data

Aug. 1, 2001 (JP) ............... P.2001-233666

(51) Int. Cl.
 *G11B 7/24* (2006.01)
(52) U.S. Cl. ............. 430/270.19; 430/270.18; 430/945; 428/64.8; 369/284
(58) Field of Classification Search ........... 430/220.15, 430/270.19, 945; 428/64.8; 564/309, 307; 369/283

See application file for complete search history.

(56) References Cited

U.S. PATENT DOCUMENTS

| | | | | |
|---|---|---|---|---|
| 4,656,121 A * | 4/1987 | Sato et al. | ............ | 430/270.19 |
| 5,248,584 A | 9/1993 | Miura et al. | | |
| 5,482,822 A * | 1/1996 | Mihara et al. | ......... | 430/270.14 |
| 5,605,732 A * | 2/1997 | Mihara et al. | ............ | 428/64.8 |
| 6,713,147 B2 * | 3/2004 | Morishima et al. | ....... | 428/64.1 |
| 2004/0166441 A1* | 8/2004 | Akiba et al. | ............ | 430/270.18 |
| 2005/0153241 A1* | 7/2005 | Mikoshiba et al. | .... | 430/270.19 |

FOREIGN PATENT DOCUMENTS

| | | | |
|---|---|---|---|
| EP | 0347183 | * | 12/1989 |
| EP | 0 568 877 A | | 11/1993 |
| EP | 962923 | * | 8/1999 |
| EP | 1090910 | * | 4/2001 |
| GB | 2 193 659 A | | 2/1988 |
| GB | 2 331 176 A | | 5/1999 |
| JP | 63-209995 | | 8/1988 |
| JP | 03-075190 | * | 3/1991 |
| JP | 03-164292 | * | 7/1991 |
| JP | 03-224793 | * | 10/1991 |
| JP | 06-220420 | * | 8/1994 |
| JP | 11-138998 | | 5/1999 |
| JP | 2000-052658 | * | 2/2000 |

OTHER PUBLICATIONS

Machine translation of JP 11-138998.*
Derwent abstract of JP 03-164292.*
Roberts et al., "Basic Principles of Organic Chemistry"(© 1969) pp. 954-956.*
Patent Abstract of Japan, vol. 1999, No. 10, Aug. 31, 1999 (JP 11-138998).

* cited by examiner

*Primary Examiner*—Martin Angebrannt
(74) *Attorney, Agent, or Firm*—Sughrue Mion, PLLC

(57) ABSTRACT

Disclosed is an optical information recording medium comprising a substrate having provided thereon a recording layer capable of recording information by laser beam irradiation, wherein the recording layer contains at least one compound represented by the following general formula (I):

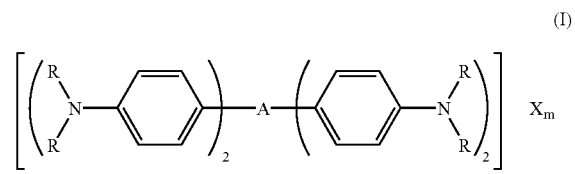

The symbols in the formula (I) are defined in the specification. Also disclosed is a method for recording optical information using the optical information recording medium.

3 Claims, No Drawings

OPTICAL INFORMATION RECORDING MEDIUM AND NOVEL IMMONIUM COMPOUND

FIELD OF THE INVENTION

The present invention relates to an optical information recording medium and a method for recording optical information. More particularly, the invention relates to a write once-type optical information recording medium which has a recording layer containing an immonium compound having a specific structure and an oxonol dye and which can record and reproduce information by laser irradiation, and to a method for recording optical information using this optical information recording medium.

BACKGROUND OF THE INVENTION

Information recording media (optical disks) which can record information only once with laser beams have hitherto been known. These information recording media are also called write once-type CDs (so-called CD-Rs), and have the advantage that a small amount of CDs can be provided at reasonable prices and promptly, compared with the production of the conventional CDs. With the recent spread of personal computers, demand for such CDs have increased. The CD-R type information recording media have the typical structure that a transparent disk-shaped substrate is laminated with a recording layer comprising an organic dye, a light reflective layer comprising a metal such as gold or silver, and a resin protective layer in this order. Information is recorded on the optical disk by irradiating a near infrared laser beam (usually, a laser beam having a wavelength of about 780 nm) to locally deform the recording layer by heat generation. On the other hand, reading (reproduction) of the information is usually carried out by irradiating a laser beam having the same wavelength as the laser beam for recording to detect the difference in reflectance between a deformed site (recorded area) of the recording layer by heat generation and a non-deformed site (non-recorded area).

In recent years, information recording media higher in recording density have been desired. In order to increase the recording density, it is effective to decrease the diameter of a laser beam irradiated. Further, it has been known a theory that a laser beam having a shorter wavelength is effective for an increase in density, because the diameter of the laser beam can be decreased. Accordingly, optical disks for carrying out recording and reproduction using laser beams having wavelengths shorter than 780 nm which has hitherto been used have been developed. For example, an optical disk called a write once-type digital versatile disk (so-called DVD-R) has been proposed. This optical disk is produced so as to provide the structure that two disks each comprising a transparent disk-shaped substrate having a diameter of 120 mm or 80 mm on which pre-grooves are formed at a track pitch of 0.7 to 0.8 µm which is narrower than 1.6 µm of the CD-R, having provided thereon a recording layer comprising a dye, and usually further a light reflective layer and a protective layer on the recording layer, or the disk and a disk-shaped protective substrate having substantially the same dimension as that of the disk are adhered to each other with an adhesive, facing the recording layer inside relative to the substrates. In the DVD-R, recording and reproduction are carried out by irradiation of a visible laser beam (usually, a laser beam having a wavelength ranging from 600 to 700 nm), and it is said that higher density recording than that of the CD-R is possible.

The DVD-R type information recording media can record information in an amount several times that of the CD-R type media. It is therefore desired that the probability of occurrence of errors in high-speed recording be small, particularly because of the necessity to rapidly process a large amount of information, not to mention that the DVD-R type media have high recording sensitivity. Further, the recording layers comprising the dyes are generally low in aging stability to heat or light, so that the development of recording layers which can maintain high performance against heat or light for a long period of time is desired.

Japanese Patent Laid-Open No. 209995/1988 discloses a CD-R type information recording medium comprising a substrate having provided thereon a recording layer comprising an oxonol dye. It is described that the use of the oxonol dye allows stable recording and reproduction characteristics to be maintained for a long period of time.

The present inventors applied the oxonol dyes described in Japanese Patent Laid-Open No. 209995/1988 to DVD-R type optical information recording media and studied their performance. The studies proved that the DVD-R type optical information recording media containing the oxonol dyes in recording layers are low in reflectance and modulation degree and are not sufficiently satisfactory in recording and reproduction characteristics. Further, the studies proved that the above-mentioned recording media are liable to develop poor reproduction in long-term exposure to light such as sunlight, so that they are insufficient in light resistance. On the other hand, Japanese Patent Laid-Open No. 138998/1999 discloses an optical information recording medium comprising a substrate having provided thereon a recording layer comprising an oxonol dye salt-bonded by a diimmonium which is a singlet oxygen quencher. It is described that the use of the oxonol dye allows stable recording and reproduction characteristics to be maintained even in long-term exposure to light such as sunlight. However, it has become clear that the optical information recording medium in which the recording layer is composed by the oxonol dye alone are liable to develop poor reproduction in long-term storage thereof under the circumstances of high temperature and humidity, and insufficient durability against heat and humidity.

SUMMARY OF THE INVENTION

It is therefore a principal object of the invention to provide an optical information recording medium having high recording characteristics and such high stability (particularly, high stability also under the circumstances of high temperature and humidity) that the recording characteristics can be sufficiently maintained for a long period of time, which can suitably record and reproduce information with a visible laser beam, Another object of the invention is to provide a method for recording information using the information recording medium.

A still other object of the invention is to provide a compound suitable for the above-mentioned information recording medium and the like.

Other objects and effects of the invention will become apparent from the following description.

The above-mentioned objects have been achieved by providing the following embodiments:

(1) An optical information recording medium comprising a substrate having provided thereon a recording layer capable of recording information by laser beam irradiation, wherein the recording layer contains at least one compound represented by the following general formula (I):

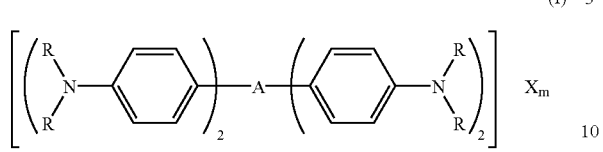

wherein R represents a hydrogen atom, an alkyl group, an aryl group or a heterocyclic group; X represents an anion; m represents 0, 1 or 2; A represents a group represented by general formula (II) or (III), wherein n represents 1 or 2; and at least one of all aromatic groups in existence is substituted by an aryl group having 6 to 18 carbon atoms, an acyl group having 2 to 18 carbon atoms, an alkylsulfonyl group having 1 to 18 carbon atoms, an arylsulfonyl group having 6 to 18 carbon atoms, an alkylsulfinyl group having 1 to 18 carbon atoms, an alkoxycarbonyl group having 2 to 18 carbon atoms, an aryloxycarbonyl group having 7 to 18 carbon atoms, an aryloxy group having 6 to 18 carbon atoms, an acyloxy group having 2 to 18 carbon atoms, a sulfonyloxy group substituted by a hydrocarbon group having 1 to 18 carbon atoms, a sulfamoyl group which may be substituted by a hydrocarbon group having 1 to 18 carbon atoms, a nitro group, a cyano group or a 4- to 7-membered heterocyclic group:

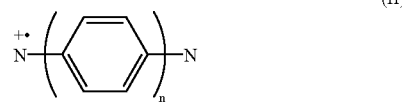

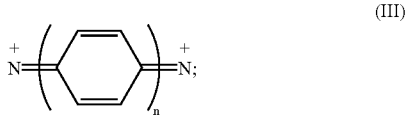

(2) The optical information recording medium according to item (1) above, wherein the recording layer further contains an oxonol dye;

(3) A compound represented by the following general formula (IV):

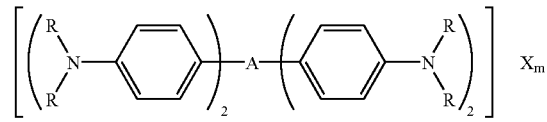

wherein R represents a hydrogen atom, an alkyl group, an aryl group or a heterocyclic group; X represents an anion; m represents 0, 1 or 2; A represents a group represented by general formula (V) or (VI), wherein n represents 1 or 2; and at least one of all aromatic groups in existence has a cyano group as a substituent group:

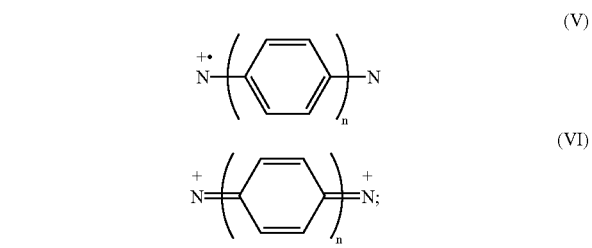

(4) The compound according to item (3) above, wherein R is a substituted or unsubstituted alkyl group, m is 1 or 2, and n is 1; and (5) The compound according to item (4) above, wherein R is an unsubstituted alkyl group having 1 to 4 carbon atoms.

The optical information recording medium of the invention has a feature that a recording layer which is provided on a substrate and capable of recording information by laser irradiation contains at least one compound represented by the above-mentioned general formula (I). Further, as a dye for recording information, an oxonol dye is preferred. Excellent recording characteristics can be exhibited not only to a laser beam in a wavelength region used for the CDRs, but also to a laser beam in a shorter wavelength region for the DVD-Rs and the like, by using the oxonol dye and the immonium compound having a specific structure represented by the above-mentioned general formula (I) as the dyes for the recording layer, and by appropriately selecting organic dyes different in absorption wavelength distribution depending on the wavelength of recording light. Further, not only light resistance is improved, but also recording and reproduction characteristics can be maintained for a long period of time even under storage conditions of high temperature and humidity. That is to say, the optical information recording medium excellent in stability can be obtained.

The optical information recording medium of the invention can have the constitution that the substrate is a transparent disk-shaped substrate having pre-grooves of a definite track pitch and the recording layer is provided on the substrate surface on which side the pre-grooves are formed. A light reflective layer comprising a metal can be further provided on the above-mentioned recording layer, and a protective layer can be provided over the recording layer.

A method for recording optical information according to the invention is a method comprising irradiating an optical information recording medium with a laser beam either within the wavelength range of 750 to 850 nm or within the wavelength range of 600 to 700 nm to record information thereon, and has a feature that information is recorded using the optical information recording medium of the above item (1) or (2). Various organic dyes can be designed as dyes excellent in recording and reproduction characteristics with respect to light either within the wavelength range of 750 to 850 nm or within the wavelength range of 600 to 700 nm, and recording can be stably carried out with good recording and reproduction characteristics for a long period of time by appropriately selecting organic dyes different in absorption wavelength distribution depending on the wavelength of recording light in the optical information recording medium.

DETAILED DESCRIPTION OF THE INVENTION

The optical information recording medium of the invention and the method for recording optical information will be described in detail below.

The optical information recording medium of the invention comprises a substrate having provided thereon a recording layer capable of recording information by laser beam irradiation, wherein the recording layer contains at least one compound represented by the above-mentioned general formula (I).

First, the compound represented by the above-mentioned general formula (I) will be described in detail.

In the above-mentioned formula, the groups represented by R, which may be the same or different, each represents a hydrogen atom, a substituted or unsubstituted, straight-chain, branched or cyclic alkyl group having 1 to 18 carbon atoms (preferably 1 to 8 carbon atoms) (for example, methyl, ethyl, propyl, isopropyl, n-butyl, isobutyl, sec-butyl, t-butyl, cyclohexyl, methoxyethyl, ethoxycarbonyl, cyanoethyl, diethylaminoethyl, hydroxyethyl, chloroethyl, acetoxyethyl, trifluoromethyl, etc.), a substituted or unsubstituted aryl group having 6 to 18 carbon atoms (preferably 6 to 10 carbon atoms) (for example, phenyl, 4-methylphenyl, 4-methoxyphenyl, etc.), or a heterocyclic group (for example, an oxazole ring, a benzoxazole ring, a thiazole ring, a benzothiazole ring, an imidazole ring, a benzimidazole ring, an indolenine ring, a pyridine ring, a morpholine ring, a piperidine ring, a pyrrolidine ring, a sulfolane ring, a furan ring, a thiophene ring, a pyrazole ring, a pyrrole ring, a chroman ring, a coumarin ring, etc.). Substituent groups of the groups represented by R include, for example, a substituted or unsubstituted, straight-chain, branched or cyclic alkyl group having 1 to 18 carbon atoms (preferably 1 to 8 carbon atoms) (for example, methyl, ethyl, propyl, isopropyl, n-butyl, isobutyl, sec-butyl, t-butyl, cyclohexyl, methoxyethyl, ethoxycarbonyl, cyanoethyl, diethylaminoethyl, hydroxyethyl, chloroethyl, acetoxyethyl, trifluoromethyl, etc.); an alkenyl group having 2 to 18 carbon atoms (preferably 2 to 8 carbon atoms) (for example, vinyl etc.); an alkynyl group having 2 to 18 carbon atoms (preferably 2 to 8 carbon atoms) (for example, vinyl etc.); a substituted or unsubstituted aryl group having 6 to 18 carbon atoms (preferably 6 to 10 carbon atoms) (for example, phenyl, 4-methylphenyl, 4-methoxyphenyl, 4-carboxyphenyl, 3,5-dicarboxyphenyl, etc.); a substituted or unsubstituted aralkyl group having 7 to 18 carbon atoms (preferably 7 to 12 carbon atoms) (for example, benzyl, carboxybenzyl, etc.); a substituted or unsubstituted acyl group having 2 to 18 carbon atoms (preferably 2 to 8 carbon atoms) (for example, acetyl, propionyl, butanoyl, chloroacetyl, etc.); a substituted or unsubstituted alkylsulfonyl or arylsulfonyl group having 1 to 18 carbon atoms (preferably 1 to 8 carbon atoms) (for example, methanesulfonyl, p-toluenesulfonyl, etc.); an alkylsulfinyl group having 1 to 18 carbon atoms (preferably 1 to 8 carbon atoms) (for example, methanesulfinyl, ethanesulfinyl, octanesulfinyl, etc.); an alkoxycarbonyl group having 2 to 18 carbon atoms (preferably 2 to 8 carbon atoms) (for example, methoxycarbonyl, ethoxycarbonyl, etc.); an aryloxycarbonyl group having 7 to 18 carbon atoms (preferably 7 to 12 carbon atoms) (for example, phenoxycarbonyl, 4-methylphenoxycarbonyl, 4-methoxyphenylcarbonyl, etc.); a substituted or unsubstituted alkoxyl group having 1 to 18 carbon atoms (preferably 1 to 8 carbon atoms) (for example, methoxy, ethoxy, n-butoxy, methoxyethoxy, etc.); a substituted or unsubstituted aryloxy group having 6 to 18 carbon atoms (preferably 6 to 10 carbon atoms) (for example, phenoxy, 4-methoxyphenoxy, etc.); an alkylthio group having 1 to 18 carbon atoms (preferably 1 to 8 carbon atoms) (for example, methylthio, ethylthio, etc.); an arylthio group having 6 to 10 carbon atoms (preferably 6 to 8 carbon atoms) (for example, phenylthio etc.); a substituted or unsubstituted acyloxy group having 2 to 18 carbon atoms (preferably 2 to 8 carbon atoms) (for example, acetoxy, ethylcarbonyloxy, cyclohexylcarbonyloxy, benzoyloxy, chloroacetyloxy, etc.); a substituted or unsubstituted sulfonyloxy group having 1 to 18 carbon atoms (preferably 1 to 8 carbon atoms) (for example, methanesulfonyloxy etc.); a substituted or unsubstituted carbamoyloxy group having 2 to 18 carbon atoms (preferably 2 to 8 carbon atoms) (for example, methylcarbamoyloxy, diethylcarbamoyloxy, etc.); an unsubstituted amino group or a substituted amino group having 1 to 18 carbon atoms (preferably 1 to 8 carbon atoms) (for example, methylamino, dimethylamino, diethylamino, anilino, methoxyphenylamino, chlorophenylamino, pyridylamino, methoxycarbonylamino, n-butoxycarbonylamino, phenoxycarbonylamino, methylcarbamoylamino, phenylcarbamoylamino, ethylthiocarbamoylamino, methylsulfamoylamino, phenylsulfamoylamino, acetylamino, ethylcarbonylamino, ethylthiocarbonylamino, cyclohexylcarbonylamino, benzoylamino, chloroacetylamino, methanesulfonylamino, benzenesulfonylamino, etc.); an amido group having 1 to 18 carbon atoms (preferably 1 to 8 carbon atoms) (for example, acetamido, acetylmethylamido, acetyloctylamido, etc.); a substituted or unsubstituted ureido group having 1 to 18 carbon atoms (preferably 1 to 8 carbon atoms) (for example, unsubstituted ureido, methylureido, dimethylureid, etc.); a substituted or unsubstituted carbamoyl group having 1 to 18 carbon atoms (preferably 1 to 8 carbon atoms) (for example, unsubstituted carbamoyl, methylcarbamoyl, ethylcarbamoyl, n-butylcarbamoyl, t-butylcarbamoyl, dimethylcarbamoyl, morpholinocarbamoyl, pyrrolidinocarbamoyl, etc.); an unsubstituted sulfamoyl group or a substituted sulfamoyl group having 1 to 18 carbon atoms (preferably 1 to 8 carbon atoms) (for example, methylsulfamoyl, phenylsulfamoyl, etc.); a halogen atom (for example, fluorine, chlorine, bromine, etc.); a hydroxyl group; a nitro group; a cyano group; a carboxyl group; and a heterocyclic group (for example, an oxazole ring, a benzoxazole ring, a thiazole ring, a benzothiazole ring, an imidazole ring, a benzimidazole ring, an indolenine ring, a pyridine ring, a morpholine ring, a piperidine ring, a pyrrolidine ring, a sulfolane ring, a furan ring, a thiophene ring, a pyrazole ring, a pyrrole ring, a chroman ring, a coumarin ring, etc.).

R is preferably a substituted or unsubstituted alkyl group, and particularly preferably an unsubstituted alkyl group having 1 to 4 carbon atoms.

X represents an anion, which may be either an inorganic anion or an organic anion. Examples thereof include an inorganic anion (for example, a fluorine ion, a chlorine ion or an iodine ion), a substituted arylsulfonate ion (for example, a p-toluenesulfonate ion or a p-chlorobenzenesulfonate ion), an aryldisulfonate ion (for example, a 1,3-benzenedisulfonate ion, a 1,5-naphthalenedisulfonate ion or a 2,6-naphthalenedisulfonate ion), an alkylsulfate ion (for example, a methylsulfate ion), a sulfate ion, a thiocyanate ion, a perchlorate ion, a hexafluorophosphate ion, a hexafluoroantimonate ion, tetrafluoroborate ion, a picrate ion, an acetate ion and a trifluoromethanesulfonate ion. Further, an ionic polymer or another anionic dye (for example, an oxonol dye) may be used.

m represents 0, 1 or 2, A represents the group represented by the above-mentioned general formula (II) or (III), and n represents 1 or 2. m is preferably 1 or 2, and n is preferably 1. In the above-mentioned general formula (I), at least one of all aromatic groups in existence is substituted by an aryl group having 6 to 18 carbon atoms, an acyl group having 2 to 18 carbon atoms, an alkylsulfonyl group having 1 to 18 carbon atoms, an arylsulfonyl group having 6 to 18 carbon atoms, an alkylsulfinyl group having 1 to 18 carbon atoms, an alkoxycarbonyl group having 2 to 18 carbon atoms, an aryloxycarbonyl group having 7 to 18 carbon atoms, an aryloxy group having 6 to 18 carbon atoms, an acyloxy group having 2 to 18 carbon atoms, a sulfonyloxy group substituted by a hydrocarbon group having 1 to 18 carbon atoms, a sulfamoyl group which may be substituted by a hydrocarbon group having 1 to 18 carbon atoms, a nitro group, a cyano group or a 4- to 7-membered heterocyclic group. Specific examples and preferred ranges thereof are the same as given for the substituent groups of the groups represented by R.

It is more preferred that the substituent groups of the aromatic rings are ones having a Hammett substituent constant ($\sigma p$) value of 0.2 or more. The Hammett substituent constant is described, for example, in *Chem. Rev.*, 91, 165 (1991). Particularly preferred examples of the substituent groups are a cyano group, a nitro group, an alkoxycarbonyl group, an acyl group, a sulfamoyl group, an alkylsulfonyl group and an arylsulfonyl group, and most preferred is a cyano group.

A position at which a hydrogen atom is substituted by the substituent group is preferably the meta-position to the carbon atom having N—(R)$_2$ as a substituent group.

Specific examples of the compounds represented by the above-mentioned general formula (I) are enumerated below, but the compounds used in the invention are not limited thereto. Of the following specific examples, Nos. 1-1 to 1-42 are also examples of the compounds represented by general formula (IV).

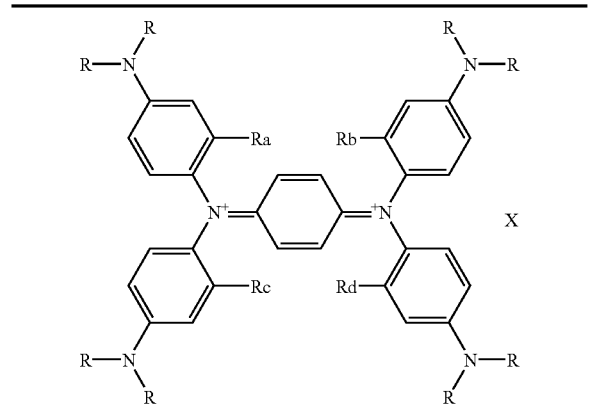

| Compound No. | X | R | Ra | Rb | Rc | Rd |
|---|---|---|---|---|---|---|
| I-1 | (PF$_6^-$)$_2$ | C$_4$H$_9$ | CN | H | H | H |
| I-2 | (PF$_6^-$)$_2$ | C$_4$H$_9$ | CN | CN | H | H |
| I-3 | (PF$_6^-$)$_2$ | C$_4$H$_9$ | CN | CN | CN | CN |
| I-4 | (PF$_6^-$)$_2$ | C$_2$H$_5$ | CN | CN | H | H |
| I-5 | (PF$_6^-$)$_2$ | C$_2$H$_5$ | CN | CN | CN | CN |
| I-6 | (PF$_6^-$)$_2$ | CH$_3$ | CN | CN | H | H |
| I-7 | (PF$_6^-$)$_2$ | CH$_3$ | CN | CN | CN | CN |
| I-8 | (PF$_6^-$)$_2$ | CH$_2$Ph | CN | CN | H | H |
| I-9 | (PF$_6^-$)$_2$ | CH$_2$Ph | CN | CN | CN | CN |
| I-10 | (ClO$_4^-$)$_2$ | C$_4$H$_9$ | CN | H | H | H |
| I-11 | (ClO$_4^-$)$_2$ | C$_4$H$_9$ | CN | CN | H | H |
| I-12 | (ClO$_4^-$)$_2$ | C$_4$H$_9$ | CN | CN | CN | CN |
| I-13 | (SbF$_6^-$)$_2$ | C$_4$H$_9$ | CN | CN | H | H |
| I-14 | (SbF$_6^-$)$_2$ | C$_4$H$_9$ | CN | CN | CN | CN |
| I-15 | (ClO$_4^-$)$_2$ | CH$_3$ | CN | CN | H | H |
| I-16 | (ClO$_4^-$)$_2$ | CH$_3$ | CN | CN | CN | CN |
| I-17 | (SbF$_6^-$)$_2$ | CH$_2$Ph | CN | CN | H | H |
| I-18 | (SbF$_6^-$)$_2$ | CH$_2$Ph | CN | CN | CN | CN |

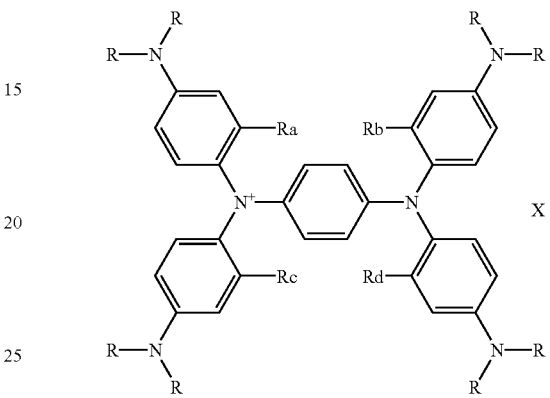

| Compound No. | X | R | Ra | Rb | Rc | Rd |
|---|---|---|---|---|---|---|
| I-19 | (PF$_6^-$) | C$_4$H$_9$ | CN | H | H | H |
| I-20 | (PF$_6^-$) | C$_4$H$_9$ | CN | CN | H | H |
| I-21 | (PF$_6^-$) | C$_4$H$_9$ | CN | CN | CN | CN |
| I-22 | (PF$_6^-$) | C$_2$H$_5$ | CN | CN | H | H |
| I-23 | (PF$_6^-$) | C$_2$H$_5$ | CN | CN | CN | CN |
| I-24 | (PF$_6^-$) | CH$_3$ | CN | CN | H | H |
| I-25 | (PF$_6^-$) | CH$_3$ | CN | CN | CN | CN |
| I-26 | (PF$_6^-$) | CH$_2$Ph | CN | CN | H | H |
| I-27 | (PF$_6^-$) | CH$_2$Ph | CN | CN | CN | CN |
| I-28 | (ClO$_4^-$) | C$_4$H$_9$ | CN | CN | H | H |
| I-29 | (ClO$_4^-$) | C$_4$H$_9$ | CN | CN | CN | CN |
| I-30 | (SbF$_6^-$) | C$_4$H$_9$ | CN | CN | H | H |
| I-31 | (SbF$_6^-$) | C$_4$H$_9$ | CN | CN | CN | CN |
| I-32 | (ClO$_4^-$) | CH$_3$ | CN | CN | H | H |
| I-33 | (ClO$_4^-$) | CH$_3$ | CN | CN | CN | CN |
| I-34 | (SbF$_6^-$) | CH$_2$Ph | CN | CN | CN | CN |

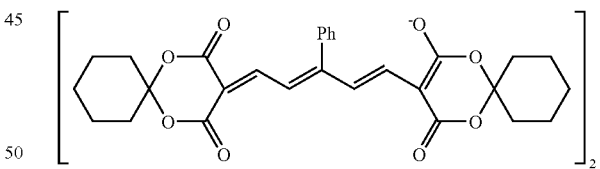

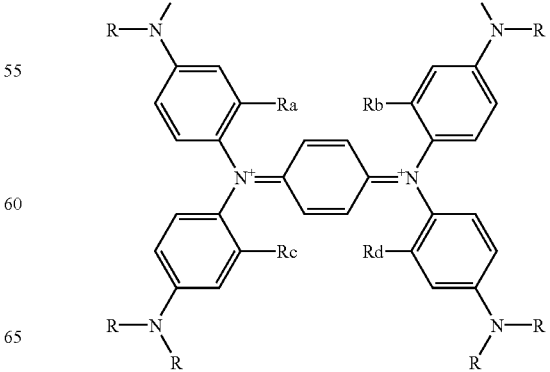

-continued

| Compound No. | R | Ra | Rb | Rc | Rd |
|---|---|---|---|---|---|
| I-35 | $C_4H_9$ | CN | H | H | H |
| I-36 | $C_4H_9$ | CN | CN | H | H |
| I-37 | $CH_3$ | CN | CN | CN | CN |
| I-38 | $CH_3$ | CN | CN | H | H |

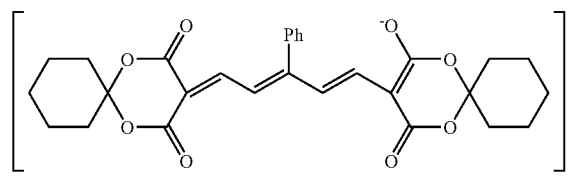

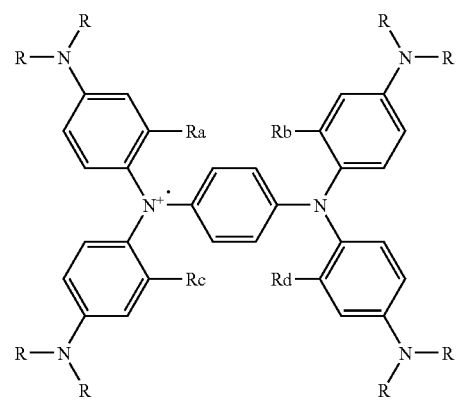

| Compound No. | R | Ra | Rb | Rc | Rd |
|---|---|---|---|---|---|
| I-39 | $C_4H_9$ | CN | H | H | H |
| I-40 | $C_4H_9$ | CN | CN | H | H |
| I-41 | $CH_3$ | CN | CN | CN | CN |
| I-42 | $CH_3$ | CN | CN | H | H |

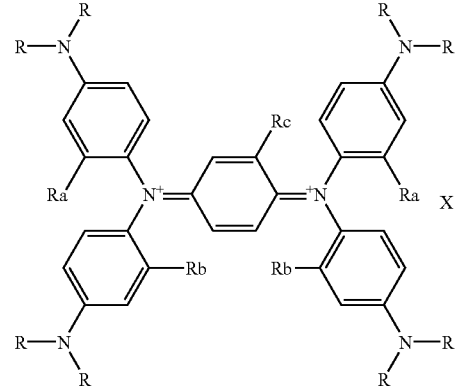

| Compound No. | R | Ra | Rb | Rc | X |
|---|---|---|---|---|---|
| I-43 | $C_4H_9$ | H | H | CN | $(PF_6^-)_2$ |
| I-44 | $C_4H_9$ | $COCH_3$ | H | H | $(PF_6^-)_2$ |
| I-45 | $CH_3$ | Ph | H | H | $(ClO_4^-)_2$ |
| I-46 | $C_4H_9$ | $SO_2CH_3$ | H | H | $(PF_6^-)_2$ |
| I-47 | $C_4H_9$ | H | H | $SOCH_3$ | $(PF_6^-)_2$ |
| I-48 | $C_4H_9$ | $CO_2CH_3$ | H | H | $(PF_6^-)_2$ |
| I-49 | $CH_3$ | Ph | H | H | $(ClO_4^-)_2$ |
| I-50 | $C_4H_9$ | $OCOCH_3$ | H | H | $(PF_6^-)_2$ |
| I-51 | $C_4H_9$ | $NO_2$ | H | H | $(PF_6^-)_2$ |
| I-52 | Ph | $SO_2N(C_2H_5)_2$ | H | H | $(ClO_4^-)_2$ |

These compounds can be synthesized by methods based on synthesis methods described in Japanese Patent Publication No. 25335/1968.

Synthesis examples of the compounds represented by general formulas (I) and (IV) will be described below.

SYNTHESIS EXAMPLES

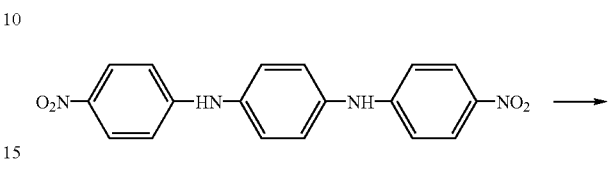

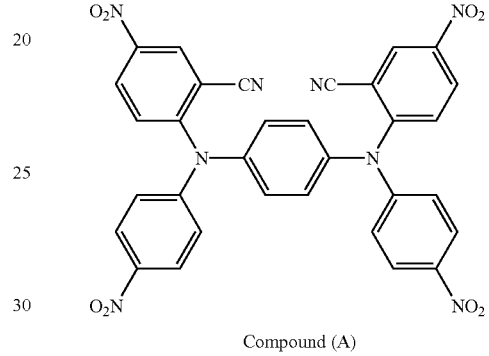

Compound (A)

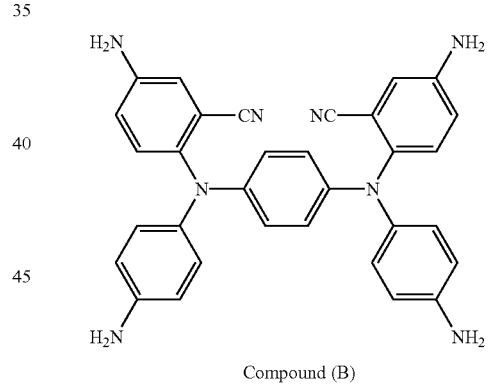

Compound (B)

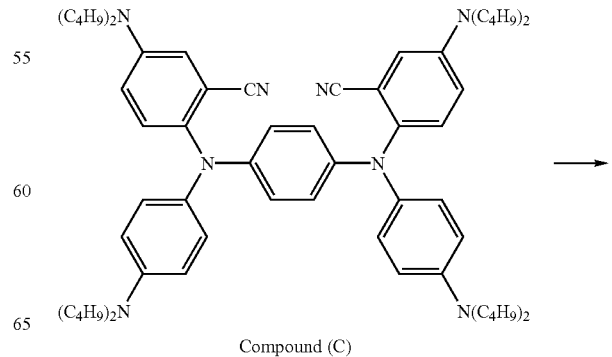

Compound (C)

-continued

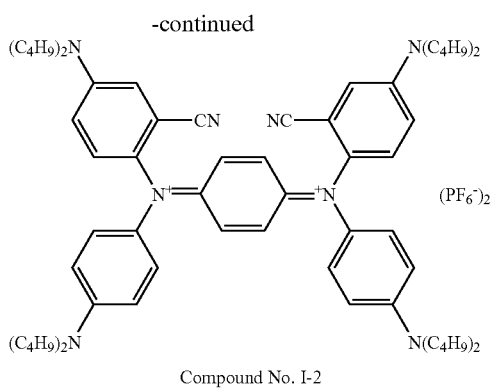

Compound No. I-2

Synthesis of Compound (A)

N,N'-Bis(p-nitrophenyl)-p-phenylenediamine (2.1 g, 6 mmol), 1-chloro-2-cyano-4-nitrobenzene (3.3 g, 0.018 mol), potassium carbonate (0.5 g, 3.6 mmol) and copper powder (0.1 g, 1.8 mmol) were suspended in DMF (10 ml), and stirred at 180° C. for 11 hours. Methanol (400 ml) was added to the reaction solution, followed by stirring at room temperature for 1 hour. Then, solid matter obtained by filtration was washed with methanol (50 ml) and water (50 ml) to obtain 3.1 g of powdered orange compound (A). This corresponds to 81% of the theoretical yield.

$^1$H-NMR (DMSO-d6): 8.8 (d, 2H), 8.6 (d, 1H), 8.4 (d, 1H), 8.3 (d, 4H), 7.6 (d, 2H), 7.2-7.4 (m, 8H)

Synthesis of Compound (C)

Ammonium chloride (0.16 g, 3.0 mmol) and reduced iron (3.8 g, 0.068 mol) were suspended in a mixed solution of acetic acid (0.56 ml), water (12 ml) and isopropanol (70 ml), followed by reflux for 30 minutes. A solution of compound (A) (2.2 g, 3.4 mmol) in DMF (40 ml) was added dropwise to this solution, followed by reflux for 8 hours. After the reaction solution was extracted with ethyl acetate, the solvents were removed by distillation under reduced pressure to obtain yellow liquid compound (B). Then, compound (B), iodobutane (7.5 g, 0.040 mol) and potassium carbonate (5.6 g, 0.040 mol) were suspended in DMF (10 ml), followed by stirring at 120° C. for 8 hours. After the reaction solution was extracted with ethyl acetate, the solvents were removed by distillation under reduced pressure to obtain 1.6 g of yellow liquid compound (C). This corresponds to 48% of the theoretical yield.

$^1$H-NMR (DMSO-d6): 7.3 (d, 4H), 6.9-7.2 (m, 12H), 6.8 (d, 2H), 3.2-3.6 (m, 16H), 1.2-1.6 (m, 32H), 0.7-1.0 (m, 24H)

Synthesis of Compound No. I-2

Compound (C) (1.6 g, 1.6 mmol) was dissolved in acetone (20 ml), and silver perchlorate (0.66 g, 2.9 mmol) was added thereto. The resulting solution was stirred at room temperature for 4 hours, and then subjected to Celite filtration. For the resulting filtrate, the solvent was removed by distillation under reduced pressure. The resulting dark blue solid was dissolved in methanol (50 ml), and ammonium hexafluorophosphate (0.52 g, 3.2 mmol) was added thereto. The resulting solution was stirred at room temperature for 2 hours, and then filtered, followed by washing with methanol to obtain 1.5 g of powdered blue compound No. I-2. This corresponds to 77% of the theoretical yield.

λmax: 850 nm (in methanol)

Synthesis of Compound No. I-20

Compound (C) (0.7 g, 0.7 mmol) was dissolved in acetone (20 ml), and silver perchlorate (0.16 g, 0.7 mmol) was added thereto. The resulting solution was stirred at room temperature for 4 hours, and then subjected to Celite filtration. For the resulting filtrate, the solvent was removed by distillation under reduced pressure. The resulting dark blue solid was dissolved in methanol (50 ml), and ammonium hexafluorophosphate (0.23 g, 1.4 mmol) was added thereto. The resulting solution was stirred at room temperature for 2 hours, and then filtered, followed by washing with methanol to obtain 0.45 g of powdered blue compound No. I-20. This corresponds to 56% of the theoretical yield.

λmax: 850 nm (in methanol)

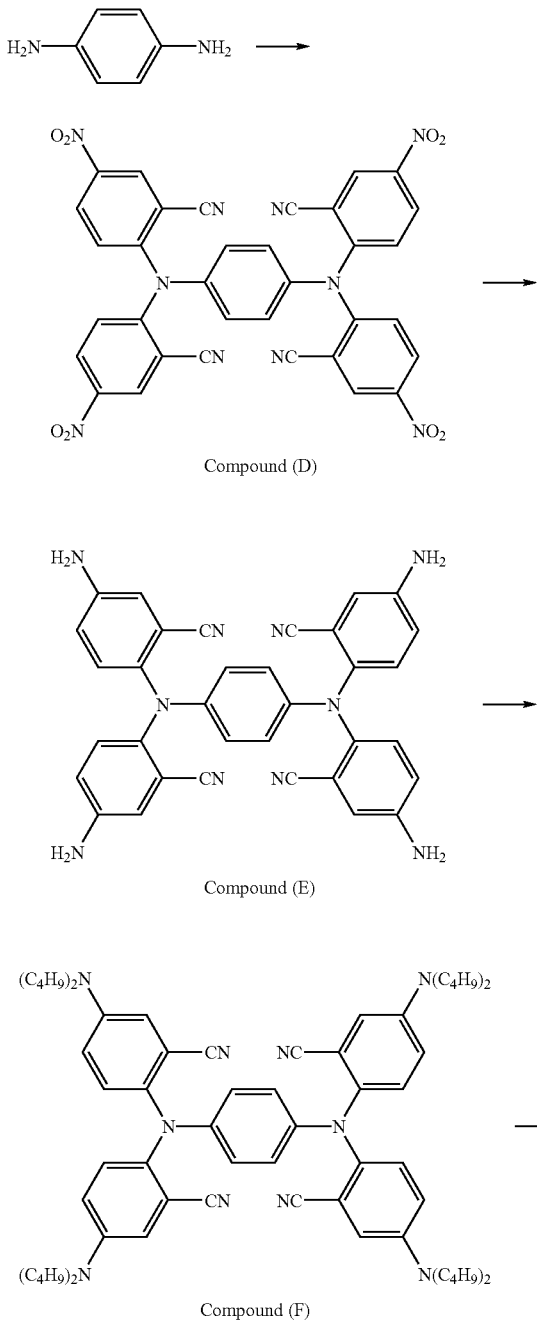

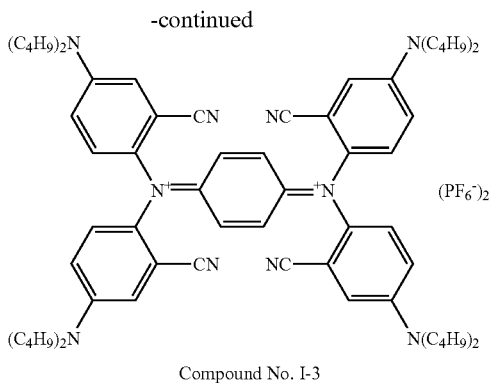

Compound No. I-3

Synthesis of Compound (D)

p-Phenylenediamine (1.1 g, 0.010 mol), 1-chloro-2-cyano-4-nitrobenzene (11 g, 0.060 mol), potassium carbonate (3.2 g, 0.023 mol) and copper powder (0.3 g, 5.4 mmol) were suspended in DMF (40 ml), and stirred at 180° C. for 16 hours. Methanol (400 ml) was added to the reaction solution, followed by stirring at room temperature for 1 hour. Then, solid matter obtained by filtration was washed with acetonitrile (50 ml) and water (50 ml) to obtain 3.2 g of powdered yellow compound (D). This corresponds to 42% of the theoretical yield.

$^1$H-NMR (DMSO-d6): 8.8 (d, 4H), 8.5 (dd, 4H), 7.5 (d, 4H), 7.3 (s, 4H)

Synthesis of Compound (F)

Ammonium chloride (0.23 g, 4.3 mmol) and reduced iron (5.4 g, 0.096 mol) were suspended in a mixed solution of acetic acid (0.79 ml), water (17 ml) and isopropanol (90 ml), followed by reflux for 30 minutes. A solution of compound (D) (3.1 g, 4.5 mmol) in DMF (40 ml) was added dropwise to this solution, followed by reflux for 8 hours. After the reaction solution was extracted with ethyl acetate, the solvents were removed by distillation under reduced pressure to obtain yellow liquid compound (E). Then, compound (E), iodobutane (8.2 ml, 0.072 mol) and potassium carbonate (9.9 g, 0.072 mol) were suspended in DMF (30 ml), followed by stirring at 120° C. for 8 hours. After the reaction solution was extracted with ethyl acetate, the solvents were removed by distillation under reduced pressure. Methanol (20 ml) was added to the resulting yellow liquid, and stirred at room temperature for 3 hours, followed by filtration to obtain 1.2 g of powdered yellow compound (F). This corresponds to 26% of the theoretical yield.

$^1$H-NMR (DMSO-d6): 7.1 (d, 4H), 6.7-6.9 (m, 12H), 3.2 (t, 16H), 1.5 (tt, 16H), 1.3 (tt, 16H), 0.9 (t, 24H)

Synthesis of Compound No. I-3

Compound (F) (1.0 g, 1.0 mmol) was dissolved in acetone (20 ml), and silver perchlorate (0.44 g, 1.9 mmol) was added thereto. The resulting solution was stirred at room temperature for 4 hours, and then subjected to Celite filtration. For the resulting filtrate, the solvent was removed by distillation under reduced pressure. The resulting dark blue solid was dissolved in methanol (50 ml), and ammonium hexafluorophosphate (0.33 g, 2.0 mmol) was added thereto. The resulting solution was stirred at room temperature for 2 hours, and then filtered, followed by washing with methanol to obtain 0.71 g of powdered dark yellow compound No. I-3. This corresponds to 54% of the theoretical yield.

λmax: 1100 nm (in methanol)

As the dye for recording, there can be used a cyanine dye, an oxonol dye, a phthalocyanine dye, a pyrromethene metal complex dye, a porphyrin dye, a pyrylium dye, an azulenium dye, a squarylium dye, a naphthoquinone dye, a triphenylmethane dye, a triallylmethane dye or the like. The oxonol dye is preferred among others.

The oxonol dye will be described below. In the invention, the oxonol dye indicates a polymethine dye having an anionic chromophore. Specific examples thereof include oxonol dyes described in Japanese Patent Laid-Open Nos. 209995/1988, 297103/1998, 309871/1998, 309872/1998, 25505/1999, 78106/1999, 138998/1999, 348420/1999 and 52658/2000 and Japanese Patent Application No. 52293/2001. In particular, examples of oxonol dyes disclosed in Japanese Patent Laid-Open No. 138998/1999 are dyes of general formulas (I-1), (I-2), (I-3), and (I-4):

General Formula (I-1)

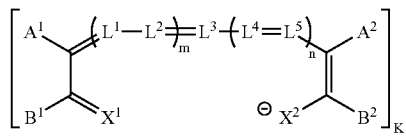

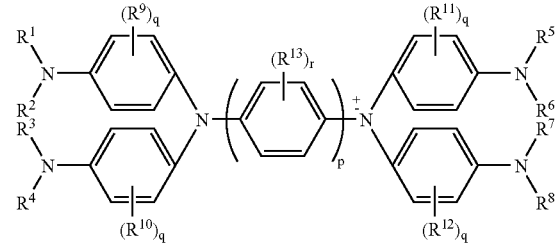

General Formula (I-2)

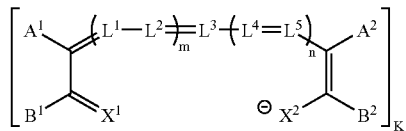

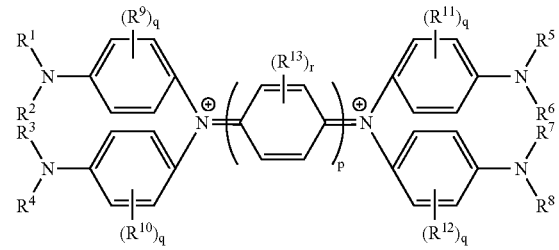

General Formula (I-3)

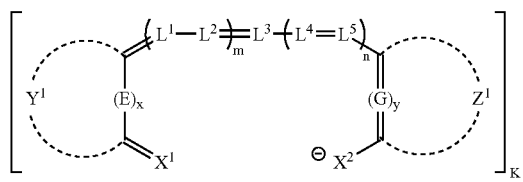

-continued

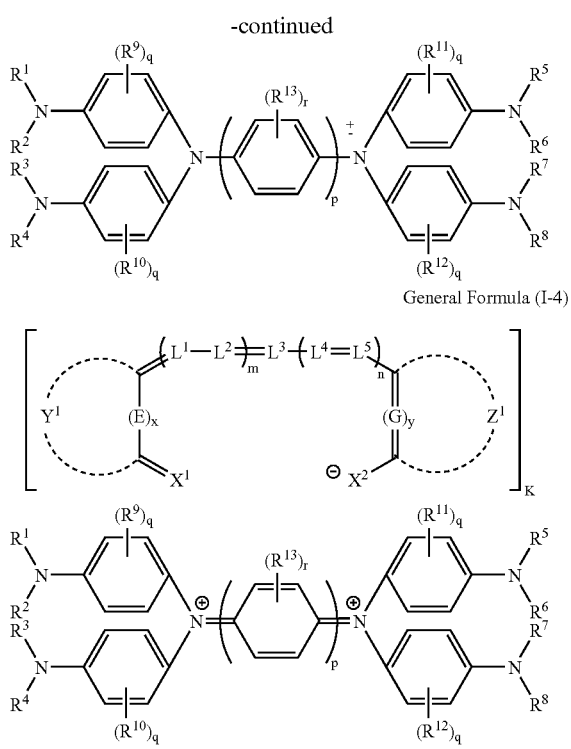

General Formula (I-4)

wherein $A^1$, $A^2$, $B^1$ and $B^2$ each independently represent a substituent; $Y^1$ and $Z^1$ each independently represent an atomic group necessary for forming a carbocyclic or heterocyclic ring; E and G each independently represent an atomic group necessary for completing a conjugated double bond chain; $X^1$ represents =O, =NR or =C(CN)$_2$; $X^2$ represents —O, —NR or —C(CN)$_2$ (provided that R represents a substituent); $L^1$, $L^2$, $L^3$, $L^4$ and $L^5$ each independently represent a methine group which may be substituted; m and n each independently represent 0, 1 or 2; x and y each independently represent 0 or 1, k represent an integer necessary for neutralizing the counter cation; $R^1$, $R^2$, $R^3$, $R^4$, $R^5$, $R^6$, $R^7$ and $R^8$ each independently represent a hydrogen atom or a substituent (provided that each combination of $R^1$ and $R^2$, $R^3$ and $R^4$, $R^5$ and $R^6$, and $R^7$ and $R^8$ may interlock with each other to form a heterocyclic ring together with the respective nitrogen atom); $R^9$, $R^{10}$, $R^{11}$, $R^{12}$ and $R^{13}$ each independently represent a substituent; p represent 1 or 2; and q and r each independently represent an integer of from 0 to 4. Additionally, a specific example of an oxonol dye described in Japanese Patent Laid-Open No. 52658/2000 is a dye of formula (I-5):

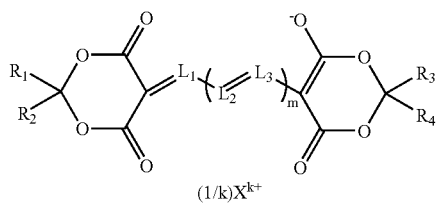

wherein $R_1$, $R_2$, $R_3$ and $R_4$ each independently represent a hydrogen atom, an alkyl group, an aryl group, an aralkyl group or a heterocyclic group, $L_1$, $L_2$ and $L_3$ each independently represent a methine group which may have a substituent, m represents 0, 1, 2 or 3, and $X^{k+}$ is an onium ion represented by formula (I-2):

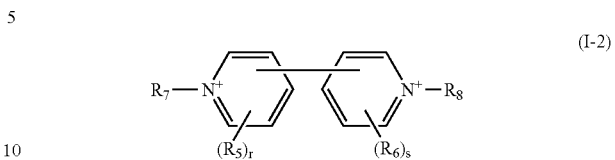

(I-2)

wherein $R_5$ and $R_6$ each independently represents a substituent, $R_7$ and $R_8$ each independently represents a substituted or unsubstituted alkyl group, a substituted or unsubstituted alkenyl group, a substituted or unsubstituted alkynyl group, a substituted or unsubstituted aralkyl group, a substituted or unsubstituted aryl group or a substituted or unsubstituted heterocyclic group, the couples of $R_5$ and $R_6$, $R_5$ and $R_7$, $R_6$ and $R_8$, $R_7$ and $R_8$ each may be combined together to form a ring, and r and s each independently represents 0 or an integer of from 1 to 4, provided that when r and s each is 2 or more, the plurality of $R_5$ or $R_6$ groups may be the same or different. Oxonol dyes described in Japanese Patent Laid-Open No. 52658/2000 and Japanese Patent Application No. 52293/2001, in which acidic nuclei have the meldrum's acid structure, are preferred because of their particularly excellent recording characteristics.

The optical information recording medium of the invention comprises a substrate having provided thereon a recording layer containing at least one compound represented by the above-mentioned general formula (I). The compound according to the invention can be advantageously used in a CD-R, a DVD-R, etc. as the optical information recording medium.

The recording layers can contain various fading inhibitors for further improving the light resistance of the recording layers. The fading inhibitors include organic oxidizing agents and singlet oxygen quenchers other than those of the invention. As the organic oxidizing agents used as the fading inhibitors, there are preferably used compounds described in Japanese Patent Laid-Open No. 151861/1998.

The compounds according to the invention may be used either alone or as a combination of two or more thereof.

Then, the structure of the information recording medium of the invention will be illustrated. As described above, there is no particular limitation on the optical information recording medium of the invention, as long as it has the substrate having provided thereon the recording layer containing at least one compound represented by the above-mentioned general formula (I). However, when the optical information recording medium of the invention is applied as the CD-R type medium, it is preferred that the recording layer containing at least one compound represented by the above-mentioned general formula (I), a light reflective layer and a protective layer are provided in this order on a transparent disk-shaped substrate having a thickness of 1.2±0.2 mm on which pre-grooves are formed at a track pitch of 1.4 µm to 1.8 µm. Further, when the optical information recording medium of the invention is applied as the DVD-R type medium, the following embodiments are preferred:

(1) An information recording medium having a thickness of 1.2±0.2 mm comprising two laminates each comprising a transparent disk-shaped substrate having provided thereon the recording layer containing at least one compound represented by the above-mentioned general formula (I) of the invention, each substrate having a diameter of 120±0.3 mm or 80±3 mm and a thickness of 0.6±0.1 mm, pre-grooves being formed on the substrate at a track pitch of 0.6 µm to 0.9 µm, the recording layer being provided on the side where the pre-grooves are formed, the laminates being adhered to each other, facing the respective recording layers inside relative to the substrates; and (2) An information recording medium having a thickness of 1.2±0.2 mm comprising a laminates comprising a transparent disk-shaped substrate having provided thereon the recording layer containing at least one compound represented by the above-mentioned general formula (I) of the invention and a disk-shaped protective plate having substantially the same size as that of the disk-shaped substrate, the substrate having a diameter of 120±0.3 mm or 80±3 mm and a thickness of 0.6±0.1 mm, pre-grooves being formed on the substrate at a track pitch of 0.6 µm to 0.9 µm, the recording layer being provided on the side where the pre-grooves are formed, the laminate being adhered to the protective plate, facing the recording layer inside relative to the substrate.

Also in the above-mentioned embodiments, it is preferred that a reflective layer is provided on the recording layer. Further, a protective layer may be provided on the reflective layer.

Methods for producing the information recording media of the invention will be described below.

For the DVD-R type recording media, the information recording media of the invention can be produced basically employing the materials used in the production of the CD-R type information recording media with the exception that substrates are used on which pre-grooves are formed at a narrower track pitch than those of the CD-R type media for attaining a higher recording density. That is to say, the DVD-R type information recording medium can be produced by preparing two laminates in each of which the recording layer, the light reflective layer, and further optionally the protective layer are formed on the substrate in this order, and adhering these two laminates to each other with an adhesive, or by similarly adhering the laminate to the disk-shaped protective substrate having substantially the same size as that of the substrate of the laminate with an adhesive.

The information recording media of the invention can be produced, for example, by the following methods. The substrates (including the protective substrates) can be arbitrarily selected from various materials used as the substrates of the conventional information recording media. The materials for the substrates include, for example, glass; polycarbonates; acrylic resins such as polymethyl methacrylate; vinyl chloride resins such as polyvinyl chloride and vinyl chloride copolymers; epoxy resins; amorphous polyolefins; polyesters; and the like. They may be used in combination as so desired. These materials can be used in the film form or in the rigid substrate form. Of the above-mentioned materials, polycarbonates are preferred in terms of moisture resistance, dimensional stability, cost and the like.

An undercoat layer may be provided on the surface of the substrate on which the recording layer is formed, for the purposes of improving planarity, enhancing adhesion and preventing deterioration of the recording layers. Materials for the undercoat layers include, for example, polymers such as polymethyl methacrylate, an acrylic acid-methacrylic acid copolymer, a styrene-maleic anhydride copolymer, polyvinyl alcohol, N-methylolacrylamide, a styrene-vinyltoluene copolymer, chlorosulfonated polyethylene, nitrocellulose, polyvinyl chloride, a chlorinated polyolefin, a polyester, a polyimide, a vinyl acetate-vinyl chloride copolymer, an ethylene-vinyl acetate copolymer, polyethylene, polypropylene and a polycarbonate; and surface modifiers such as a silane coupling agent. The undercoat layer can be formed by dissolving or dispersing the above-mentioned material in an appropriate solvent to prepare a coating solution, and applying the resulting coating solution to the surface of the substrate by a coating method such as spin coating, dip coating or extrusion coating. The thickness of the undercoat layer is generally within the range of 0.005 µm to 20 µm, and preferably within the range of 0.01 µm to 10 µm.

Grooves for tracking or unevenness (pre-grooves) for expressing information such as address signals are usually formed on the substrate (or undercoat layer). It is preferred that these pre-grooves are directly formed on the substrate at the above-mentioned track pitch at the time of injection molding or extrusion molding of the resin material such as the polycarbonate. The pre-grooves may be formed by providing a pre-groove layer. As a material for the pre-groove layer, there can be used a mixture of at least one monomer (or oligomer) selected from a monoester, a diester, a triester and a tetraester of acrylic acid, and a photopolymerization initiator. The pre-groove layer is formed, for example, by applying a mixed solution comprising the above-mentioned acrylic acid ester and the photopolymerization initiator onto a mother die (stamper) precisely fabricated, further placing the substrate on the resulting coated layer, then irradiating the coated layer with ultraviolet rays through the substrate or the mother die, thereby curing the coated layer to fixedly adhere the coated layer to the substrate, and thereafter separating the substrate from the mother die. The thickness of the pre-groove layer is generally within the range of 0.05 µm to 100 µm, and preferably within the range of 0.1 µm to 50 µm.

The depth of the pre-grooves preferably ranges from 300 angstroms to 2000 angstroms, and the half-width thereof preferably ranges from 0.2 µm to 0.9 µm. The use of the pre-grooves having a depth ranging from 1500 angstroms to 2000 angstroms can improve the sensitivity without a substantial reduction in reflectance, which is particularly advantageous to the CD-R type recording media.

The recording layer comprising the dye compound represented by the above-mentioned formula according to the invention is provided on the surface of the substrate (or undercoat layer) on which the pre-grooves are formed.

The recording layer can be formed by dissolving the dye according to the invention, and further optionally the quencher and a binder in a solvent to prepare a coating solution, and then, applying the coating solution onto the surface of the substrate to form a coating film, followed by drying. The solvents for the coating solutions for the formation of the dye recording layers include esters such as methyl lactate, ethyl lactate, butyl acetate and cellosolve acetate; ketones such as methyl ethyl ketone, cyclohexanone and methyl isobutyl ketone; chlorinated hydrocarbons such as dichloromethane, 1,2-dichloroethane and chloroform; amides such as dimethylformamide; hydrocarbons such as cyclohexane; ethers such as tetrahydrofuran, ethyl ether and dioxane; alcohols such as ethanol, n-propanol, isopropanol, n-butanol and diacetone alcohol; fluorine solvents such as 2,2,3,3-tetrafluoropropanol; and glycol ethers such as ethylene glycol monomethyl ether, ethylene glycol monoethyl ether and propylene glycol monomethyl ether. The above-mentioned solvents can be used either alone or as a combination of two or more thereof, considering the solubility of the dyes to be used. Various additives such as an antioxidant, an UV absorber, a plasticizer and a lubricant may be further added to the coating solution, depending on their purpose.

Examples of the binders include natural organic polymers such as gelatin, a cellulose derivative, dextran, rosin and rubber; and synthetic organic polymers such as hydrocarbon resins such as polyethylene, polypropylene, polystyrene and polyisobutylene; vinyl resins such as polyvinyl chloride, polyvinylidene chloride and a vinyl chloride-vinyl acetate copolymer; acrylic resins such as polymethyl acrylate and polymethyl methacrylate; polyvinyl alcohol; chlorinated polyethylene; epoxy resins; butyral resins; rubber derivatives; and initial condensation products of thermosetting resins such as a phenolformaldehyde resin. When the binder is used as the material for the recording layer in combination with the dye, the amount of the binder used is generally within a range of 0.01 to 50 time (by weight ratio), preferably within a range of 0.1 to 5 time (by weight ratio), the amount of the dye. The concentration of the coating solution thus prepared is generally within the range of 0.01% to 10% by weight, and preferably within the range of 0.1% to 5% by weight.

Coating methods include spraying, spin coating, dip coating, roll coating, blade coating, doctor roll coating, screen printing and the like. The recording layer may be either a monolayer or a multilayer. The thickness of the recording layer is generally within the range of 20 to 500 nm, and preferably within the range of 50 to 300 nm.

The reflective layer is provided on the recording layer for the purpose of improving the reflectance in the reproduction of information. Light reflective materials, materials for the reflective layer, are materials having high reflectance to the laser beams, and examples thereof include metals and semimetals such as Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn and Bi, and stainless steel. Of these, preferred are Cr, Ni, Pt, Cu, Ag, Au, Al and stainless steel. These materials may be used either alone or as a combination of two or more thereof. Further, they may also be used as alloys. The reflective layer can be formed on the recording layer, for example, by vapor deposition, sputtering or ion plating of the above-mentioned reflective material. The thickness of the reflective layer is generally within the range of 10 to 300 nm, and preferably within the range of 50 to 200 nm.

On the reflective layer, the protective layer may be provided for the purpose of protecting the recording layers physically and chemically. The protective layer may also be provided on the side where no recording layer is provided, for the purposes of enhancing scratch resistance and moisture resistance. Examples of materials used in the protective layer include inorganic materials such as SiO, $SiO_2$, $MgF_2$, $SnO_2$ and $Si_3N_4$, and organic materials such as a thermoplastic resin, a thermosetting resin and an UV-curing resin. The protective layer can be formed, for example, by laminating the reflective layer and/or the substrate with a film obtained by extrusion of a plastic through an adhesive layer. Alternatively, it may be provided by a method such as vacuum vapor deposition, sputtering or coating. In the case of the thermoplastic resin or the thermosetting resin, the protective layer can also be formed by dissolving the resin in an appropriate solvent to prepare a coating solution, and then, applying the resulting coating solution, followed by drying. In the case of the UV-curing resin, the resin can be applied as such, or dissolved in an appropriate solvent to prepare a coating solution, which are applied, followed by irradiation of UV light to cure the resin, thereby forming the protective layer. Various additives such as an antistatic agent, an antioxidant and an UV absorber may be added to the coating solution depending on its purpose. The thickness of the protective layer is generally within the range of 0.1 to 100 μm. According to the above-mentioned process, the laminate comprising the substrate having provided thereon the recording layer, the light reflective layer and the protective layer can be produced. The DVD-R type information recording medium having two recording layers can be produced by adhering the two laminates produced as described above to each other, facing the respective recording layers inside relative to the substrates. Means for adhering the laminates include a method using a slow-acting ultraviolet curing adhesive, a hot melt method and a method of adhering the laminates with an adhesive tape. From the viewpoints of damages to the recording layer and cost, the method using the slow-acting ultraviolet curing adhesive is preferred. As the adhesive, a solventless adhesive is preferably used. Coating methods of the adhesive include spraying, spin control coating, roll coating, screen printing and the like. Of these, screen printing is preferred. Further, the DVD-R type information recording medium having a recording layer only on one side can be produced by adhering the laminate to the disk-shaped protective substrate having substantially the same size as that of the substrate of the laminate with the adhesive, facing the recording layer inside relative to the substrate.

The information recording method of the invention is conducted using the above-mentioned information recording medium, for example, in the following manner. First, the information recording medium is irradiated from the substrate side thereof with light for recording such as a semiconductor laser beam, while rotating the medium at a constant linear speed (1.2 to 14 m/second for the CD format) or at a constant angular speed. It is considered that this light irradiation results in the formation of voids in the interface of the recording layer and the reflective layer (the voids are formed, accompanying the deformation of the recording layer or the reflective layer, or the deformation of both layers), or in the building-up deformation of the substrate, or results in changes in the discoloration or the association state of the recording layer, whereby there occurs a change of the reflectance to cause recording of information. As the recording light, there is used a laser beam in the visible light region, that is to say, in the case of the CD-R type recording medium, a semiconductor laser beam having a center oscillation wavelength of 780 nm. In the case of the DVD-R type recording medium, a laser beam having an oscillation wavelength ranging from 600 nm to 700 nm (preferably from 620 to 680 nm, and more preferably from 630 to 660 nm) is generally used. The information recorded as described above can be reproduced by irradiating the information recording medium from the substrate side thereof with a semiconductor laser beam having the same wavelength as the laser beam used in recording, while rotating the medium at the same constant linear speed as described above, and detecting the reflective light thereof.

EXAMPLES

The present invention will be illustrated in greater detail with reference to the following Examples, but the invention should not be construed as being limited thereto.

Example 1

A polycarbonate resin was formed into a 0.6-mm thick, 120-mm diameter substrate having spiral pre-grooves (depth: 150 nm, width: 290 nm, track pitch: 0.74 μm) by use of an injection molding machine (manufactured by Sumitomo Heavy Industries, Ltd.). The above-mentioned compound (I-2) and oxonol dye (A) described below was dissolved at a weight ratio of 1:20 in 100 ml of 2,2,3,3-tetrafluoropropanol to prepare a coating solution (dye concentration: 1% by weight). This coating solution was applied by spin coating onto a surface of the substrate on which the spiral pre-grooves were formed to form a dye layer. At this time, the thickness of the dye layer was 80 nm. Subsequently, silver was sputtered on the dye layer to form a reflective layer having a thickness of about 150 nm. Then, an ultraviolet curing resin (DAICURE CLEAR SD-318, manufactured by Dainippon Ink & Chemicals, Inc.) was applied onto the reflective layer by spin coating, and irradiated with ultraviolet rays by use of a metal halide lamp to form a protective layer having a thickness of about 7 μm, thus obtaining a 0.6-mm thick disk A. Separately, silver was sputtered on the substrate without coating with the dye coating solution, and the protective layer was formed thereon to form a 0.6-mm thick disk B having no dye recording layer. The disk A and the disk B were adhered to each other to form one disk in the following manner. First, a slow-acting cationic polymerization type adhesive (SK 7000, manufactured by Sony Chemicals Corp.) was applied onto the protective layers of the disk A and the disk B by screen printing. The mesh size of a screen printing plate used at this time was 300 meshes. Then, immediately after irradiation with ultraviolet rays by use of a metal halide lamp, the disk A and the disk B were adhered to each other, facing the respective protective layers inside, and pressed from both sides. After standing for about 5 minutes, the adhesive was completely cured to complete one disk having a thickness of 1.2 mm.

Oxonol dye (A): Specific example (I-15) described in Japanese Patent Application No. 52293/2000

Examples 2 to 8 and Comparative Examples 1 to 4

DVD-R type disks of Examples 2 to 8 and Comparative Examples 1 to 4 were obtained in the same manner as in Example 1 with the exception that the above-mentioned compound (I-2) and oxonol dye (A) were substituted by compounds shown in Table 1 (the mixing ratio and the amount used were not changed).

Evaluation as Optical Disk

Signals were recorded on each of the DVD-R type optical disks of Examples and Comparative Examples with a DDU 1000 evaluating device (manufactured by Pulstec Industrial Co., Ltd.) using a laser beam having a wavelength of 655 nm (pick up to Na 0.6), a constant line speed of 3.49 m/s, a modulation frequency of 4 MHz and a recording power of 9 mW. Then, using a laser beam having the same wavelength as the recording laser beam, the signal was reproduced at a laser power of 0.5 mW, and the modulation degree of 14T and the jitter were measured.

Light Resistance:

Each sample having subjected to recording as described above was irradiated for 72 hours using a Xe lamp (170,000 luxes), and the modulation degree and the jitter after irradiation were measured in the same manner as described above.

The evaluation results obtained are shown in Table 1.

Durability against Heat and Humidity:

Each sample having subjected to recording as described above was stored for 72 hours under circumstances of a high temperature of 80° C. and a high humidity of 85%, and the modulation degree and the jitter after storage were measured in the same manner as described above.

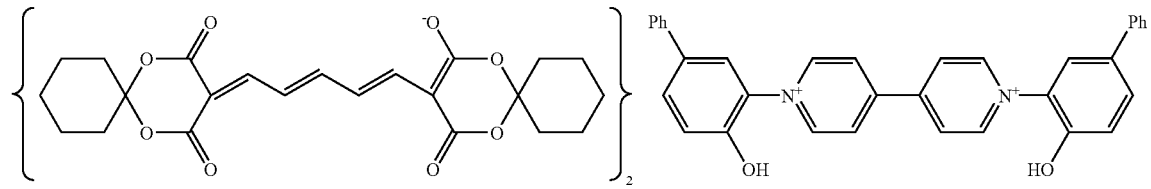

The evaluation results obtained are shown in Table 1.

TABLE 1

| | Compound Used in Recording Layer | | Recording and Reproduction Characteristics (before storage) | | Recording and Reproduction Characteristics (after Xe lamp irradiation) | | Recording and Reproduction Characteristics (after storage at 80° C., 85%) | |
|---|---|---|---|---|---|---|---|---|
| | | | 14T | Jitter | 14T | Jitter | 14T | Jitter |
| Example 1 | (I-2) | (A) | 62 | 6.8 | 66 | 7.0 | 60 | 7.0 |
| Example 2 | (I-14) | (A) | 61 | 6.9 | 68 | 7.2 | 57 | 7.5 |
| Example 3 | (I-20) | (A) | 62 | 6.8 | 68 | 7.3 | 59 | 8.0 |
| Example 4 | (I-24) | (A) | 62 | 6.8 | 66 | 7.0 | 60 | 7.0 |
| Example 5 | (I-44) | (A) | 61 | 7.2 | 69 | 7.8 | 59 | 7.8 |
| Example 6 | (I-2) | (B) | 56 | 7.6 | 64 | 8.2 | 55 | 7.9 |
| Example 7 | (I-2) | (C) | 53 | 8.9 | 68 | 10.1 | 51 | 10.1 |
| Example 8 | (I-2) | (D) | 64 | 9.2 | 76 | 11.6 | 50 | 11.4 |
| Comparative Example 1 | (IRG-023) | (A) | 62 | 7.5 | 67 | 8.3 | 52 | 10.2 |

TABLE 1-continued

| | Compound Used in Recording Layer | Recording and Reproduction Characteristics (before storage) | | Recording and Reproduction Characteristics (after Xe lamp irradiation) | | Recording and Reproduction Characteristics (after storage at 80° C., 85%) | |
|---|---|---|---|---|---|---|---|
| | | 14T | Jitter | 14T | Jitter | 14T | Jitter |
| Comparative Example 2 | (IRG-023) (B) | 56 | 8.3 | 70 | 9.2 | 48 | 10.8 |
| Comparative Example 3 | (IRG-023) (C) | 53 | 8.0 | 70 | 12.2 | 38 | Impossible to measure |
| Comparative Example 4 | (IRG-023) (D) | 62 | 9.4 | 77 | 12.0 | 48 | Impossible to measure |

Compounds Used in Examples 6 to 8 and Comparative Examples 1 to 4:

Oxonol dye (B): Specific example (Dye 79) described in Japanese Patent Laid-Open No. 52658/2000

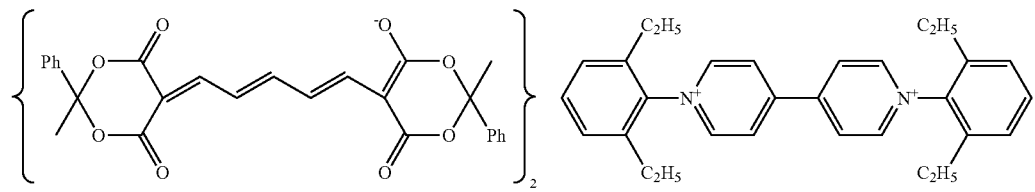

Oxonol dye (C): Specific example (Dye 73) described in Japanese Patent Laid-Open No. 309872/1998

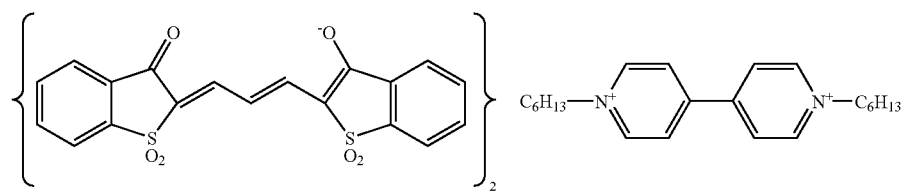

Cyanine dye (D): Specific example (KA 10) described in Japanese Patent Laid-Open No. 181211/1998

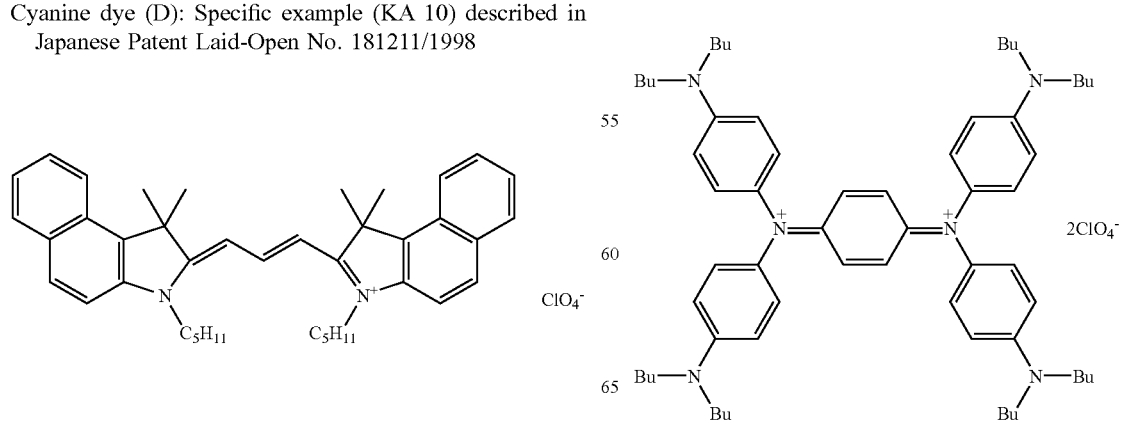

IRG-023: Manufactured by Nippon Kayaku Co., Ltd.

The above-mentioned compound IRG-023 for comparison is a compound generally known as a quencher. As can be seen from the results shown in Table 1, the DVD-R type optical disks having a recording layer containing at least one compound represented by the above-mentioned general formula (I) according to the invention (Examples 1 to 8) maintain good recording and reproduction characteristics after execution of the light resistance test and the heat and humidity durability test, compared to the disks for comparison (Comparative Examples 1 to 4), which shows that the disks of the invention are excellent in light resistance and heat and humidity durability.

According to the invention, there are provided write once-type optical information recording media excellent in recording and reproduction characteristics and storage stability, in which recording and reproduction of information can be performed by laser beam irradiation. Further, there are provided optical information recording methods using the optical information recording media, giving excellent recording and reproduction characteristics and storage stability.

While the invention has been described in detail and with reference to specific examples thereof, it will be apparent to one skilled in the art that various changes and modifications can be made therein without departing from the spirit and scope thereof.

What is claimed is:

1. An optical information recording medium comprising a substrate having provided thereon a recording layer capable of recording information by laser beam irradiation, wherein the recording layer contains:

an oxonol dye represented by formula (I-5):

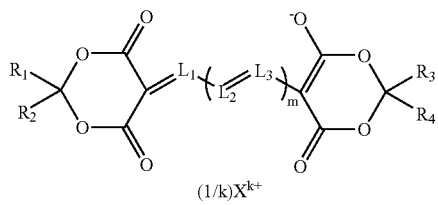

wherein $R_1$, $R_2$, $R_3$ and $R_4$ each independently represent a hydrogen atom, an alkyl group, an aryl group, an aralkyl group or a heterocyclic group, $L_1$, $L_2$ and $L_3$ each independently represent a methine group which may have a substituent, m represents 0, 1, 2 or 3, and $X^{k+}$ is an onium ion represented by formula (I-2):

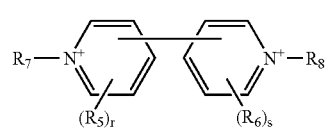

wherein $R_5$ and $R_6$ each independently represents a substituent, $R_7$ and $R_8$ each independently represents a substituted or unsubstituted alkyl group, a substituted or unsubstituted alkenyl group, a substituted or unsubstituted alkynyl group, a substituted or unsubstituted aralkyl group, a substituted or unsubstituted aryl group or a substituted or unsubstituted heterocyclic group, the couples of $R_5$ and $R_6$, $R_5$ and $R_7$, $R_6$ and $R_8$, and $R_7$ and $R_8$ each may be combined together to form a ring, and r and s each independently represents 0 or an integer of from 1 to 4, provided that when r and s each is 2 or more, the plurality of $R_5$ or $R_6$ groups may be the same or different; and at least one compound represented by the following general formula (I):

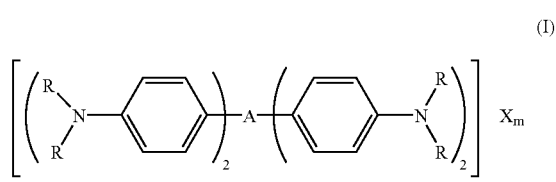

wherein R represents a hydrogen atom, an alkyl group, an aryl group or a heterocyclic group; X represents an anion; m represents 0, 1 or 2; A represents a group represented by general formula (II) or (III), wherein n represents 1; and at least one of all aromatic groups in existence is substituted by an aryl group having 6 to 18 carbon atoms, an acyl group having 2 to 18 carbon atoms, an alkylsulfonyl group having 1 to 18 carbon atoms, an arylsulfonyl group having 6 to 18 carbon atoms, an alkylsulfinyl group having 1 to 18 carbon atoms, an alkoxycarbonyl group having 2 to 18 carbon atoms, an aryloxycarbonyl group having 7 to 18 carbon atoms, an aryloxy group having 6 to 18 carbon atoms, an acyloxy group having 2 to 18 carbon atoms, a sulfonyloxy group substituted by a hydrocarbon group having 1 to 18 carbon atoms, a sulfamoyl group which may be substituted by a hydrocarbon group having 1 to 18 carbon atoms, a nitro group, a cyano group or a 4- to 7-membered heterocyclic group:

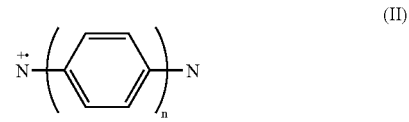

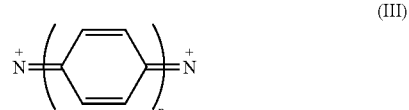

and wherein at least one of the substituents on the aromatic groups is a cyano or an acetyl group and is positioned at the meta-position relative to the carbon atom having $N—(R)_2$ as a substituent group.

2. The optical information recording medium according to claim 1, wherein said at least one of the substituents on the aromatic groups of the compound represented by formula (I) is a cyano group.

3. The optical information recording medium according to claim 1, wherein the compound represented by general formula (I) is compound (I-2), (I-14), (I-20) or (I-24):
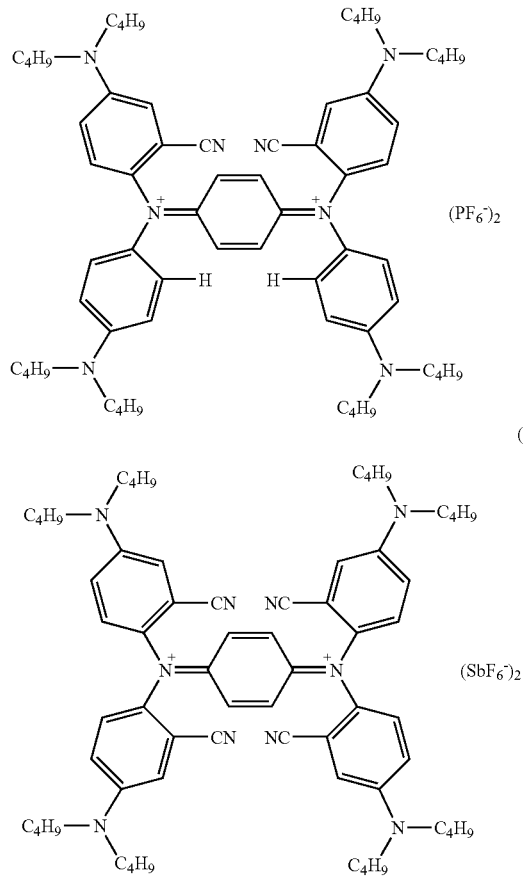
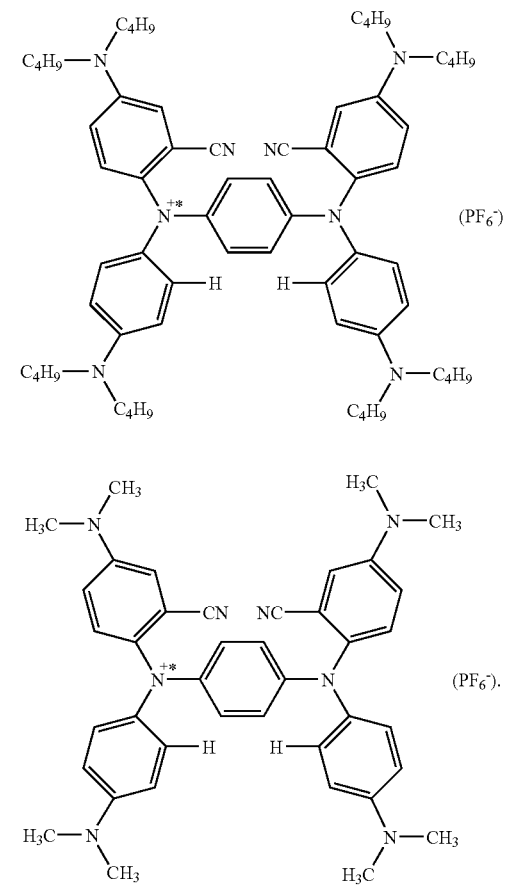
* * * * *